United States Patent
Foreman et al.

(10) Patent No.: US 6,831,469 B2
(45) Date of Patent: Dec. 14, 2004

(54) MICROPOWER APPARATUS FOR LOW IMPEDANCE MEASUREMENTS

(75) Inventors: Donald S. Foreman, Fridley, MN (US); Russell D. Braunling, Eden Prarie, MN (US); Darryl J. Wrest, Coon Rapids, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/383,689

(22) Filed: Mar. 10, 2003

(65) Prior Publication Data

US 2004/0178806 A1 Sep. 16, 2004

(51) Int. Cl.[7] .............................................. G01R 27/08
(52) U.S. Cl. ..................................................... 324/691
(58) Field of Search ................................ 324/691, 704, 324/700, 602, 603, 693; 327/182, 548

(56) References Cited

U.S. PATENT DOCUMENTS

| | | | |
|---|---|---|---|
| 3,854,087 A | | 12/1974 | Frenck et al. |
| 4,498,044 A | * | 2/1985 | Horn .......................... 324/691 |
| 5,339,025 A | * | 8/1994 | Jones et al. ................. 324/71.6 |
| 5,627,476 A | * | 5/1997 | Chambers ................... 324/704 |
| 5,811,999 A | * | 9/1998 | Hall et al. ................... 327/156 |
| 5,854,557 A | * | 12/1998 | Tiefnig ........................ 324/700 |
| 6,323,661 B1 | * | 11/2001 | Wildes et al. ............... 324/719 |
| 6,346,854 B1 | * | 2/2002 | Heithoff ...................... 330/149 |

OTHER PUBLICATIONS

PCT/US2004/007228, filed Aug. 12, 2004 by Honeywell.

* cited by examiner

*Primary Examiner*—Anjan Deb
*Assistant Examiner*—Jeff Natalini
(74) *Attorney, Agent, or Firm*—Shaw Pittman LLP

(57) ABSTRACT

A micropower apparatus and method for milliohm resistance detection includes a drive circuit and a monitoring circuit. The drive circuit includes a step up current transformer that is driven by a square wave oscillator via a low pass filter and voltage-driven current source. The drive circuit drives a series arranged test coupon and reference coupon, the latter being exposed to the elements. The coupons are Kelvin connected to the monitoring circuit, which includes a pair of low noise, low offset pre-amplifiers, a pair of post amplifiers connected to outputs of the pair of pre-amplifiers, a pair of full wave rectifiers connected to outputs of the pair of post amplifiers, and a pair of low pass filters connected to the outputs of the pair of full-wave rectifiers. Resistance values of the test and reference coupons can accordingly be monitored ratiometrically to determine a state of a selected environment by, for example, detecting changes in electrical resistance due to corrosion of the test coupon.

23 Claims, 4 Drawing Sheets

MICROPOWER APPARATUS FOR LOW IMPEDANCE MEASUREMENTS

This invention was made with Government support under contract no. N00014-02-C-0147 awarded by the Office of Naval Research. The Government has certain rights in the invention.

BACKGROUND

1. Field of the Invention

The present invention relates to a micropower instrument of high accuracy to perform ratiometric measurement of milli-ohm level resistances using milliamp-level current. The invention can be used for general environmental monitoring including, but not limited to, corrosion measurement, strain measurement and other monitoring uses that rely on ratiometric comparisons of a milli-ohm sense resistance to a milli-ohm reference resistance.

2. Background of the Invention

Corrosion can lead to failures in infrastructure, machines, and mission critical systems. Such failures are expensive to repair, can lead to lost or contaminated products, can cause environmental damage, and ultimately, can even cause unsafe environments or situations for humans. Decisions regarding the future integrity of a structure or its components depend substantially upon an accurate assessment of the conditions affecting its corrosion and rate of deterioration. Only with accurate information in hand, can an owner or operator make an informed decision as to the type, cost, and urgency of repair or replacement.

Corrosion monitoring is particularly important in areas that cannot be readily inspected visually or are difficult to inspect due to the inherent structural arrangement of a particular device, machine or structure. For example, there may be cavities within vehicles that are generally not accessible because of equipment or other structures that block an opening to the cavity. Nevertheless, corrosion monitoring of such spaces is desirable, and perhaps critical.

One well-known method of monitoring corrosion is the electrical resistance technique. This technique effectively measures material loss, i.e., corrosion, by measuring a change in electrical resistance of a metallic element, which is exposed to a selected environment, with respect to a reference element that is arranged to be immune from that environment's corrosive effects. While this technique is very popular and has found wide acceptance, the technique requires the availability of electric power. In some cases, power for the electric resistance technique is obtained from a battery. However, since it is often desirable to monitor environments for relatively long periods of time, battery life becomes an issue for these instruments. Accordingly, there is need for a micropower instrument with greatly-improved battery life and accuracy.

BRIEF SUMMARY OF THE INVENTION

The present invention provides a micropower instrument of high accuracy to perform ratiometric measurement of milli-ohm level resistances using milliamp-level current. The invention can be used for general environmental monitoring including, but not limited to, corrosion measurement, strain measurement and other monitoring uses that rely on ratiometric comparisons of a milli-ohm sense resistance to a milli-ohm reference resistance. The apparatus in accordance with the present invention is an analog measurement instrument that consumes an extremely low amount of power (thereby providing longer battery life), has high precision and accuracy, and, in a preferred embodiment, operates on and measures the resistance of a sacrificial electrical resistance coupon. The instrument is able to detect and monitor resistance in the mili ohm range.

In accordance with a corrosion detection implementation of the present invention, corrosion is measured by comparing the resistance of a corroding "test coupon" to a protected "reference" coupon that was identical or nearly so at the time of manufacture. The resistances of these coupons are very low, typically on the order of a few milliohms. Because low average power consumption is a desirable feature, high-current excitation of the coupons is not an option. On the other hand, low-current excitation results in signals of microvolt magnitude. The present invention was developed in view of the fact that available commercial instruments fail, by a wide margin, to meet low-power requirements for an environmental analysis detection system that is intended to be located or positioned in places that may generally be inaccessible, or that need to be "on-station" for long periods of time.

Features of the present invention include, but are not limited to:

- the use of AC current to excite the coupons to avoid errors due to DC offset in amplifiers and thermoelectric potentials at various connection points;
- the use of a 10:1 current step-up transformer in a drive circuit to gain a tenfold increase in power efficiency in driving the very low-impedance load (the coupons);
- the use of very low-noise, low-offset, high-gain instrumentation operational amplifiers in a first signal-processing stage; and
- the use of ratiometric measurement by current driving the reference and sensor coupons in series, sensing and signal-processing their responsive voltages, and taking the ratio of these voltages in subsequent digital signal processing.

The present invention can also be employed as a resistive straingage. More specifically, the present invention provides an instrument that can be used to monitor straingages or other resistances that are proportional to strain. The term "straingage" commonly refers to a resistive element that changes resistance with strain. Resistive straingages are routinely used for measurements of strain in structural elements or members. Such straingages have relatively high resistance to aid in ease of instrumentation, but they are relatively delicate, fragile, and require considerable care and skill to affix. They are often configured or arranged as bridges to facilitate ratiometric measurement. The ability to measure very low resistances with a micropower instrument in accordance with the present invention makes it possible to observe strain in a metal structural member (as in a sheet-metal skin) by directly measuring changes in resistance between various points in the strained member itself, obviating the need for straingages.

The features and attendant advantages of the present invention will be more fully appreciated upon a reading of the following detailed description in conjunction with the accompanying drawings.

DETAILED DESCRIPTION OF THE INVENTION

Figure 1:
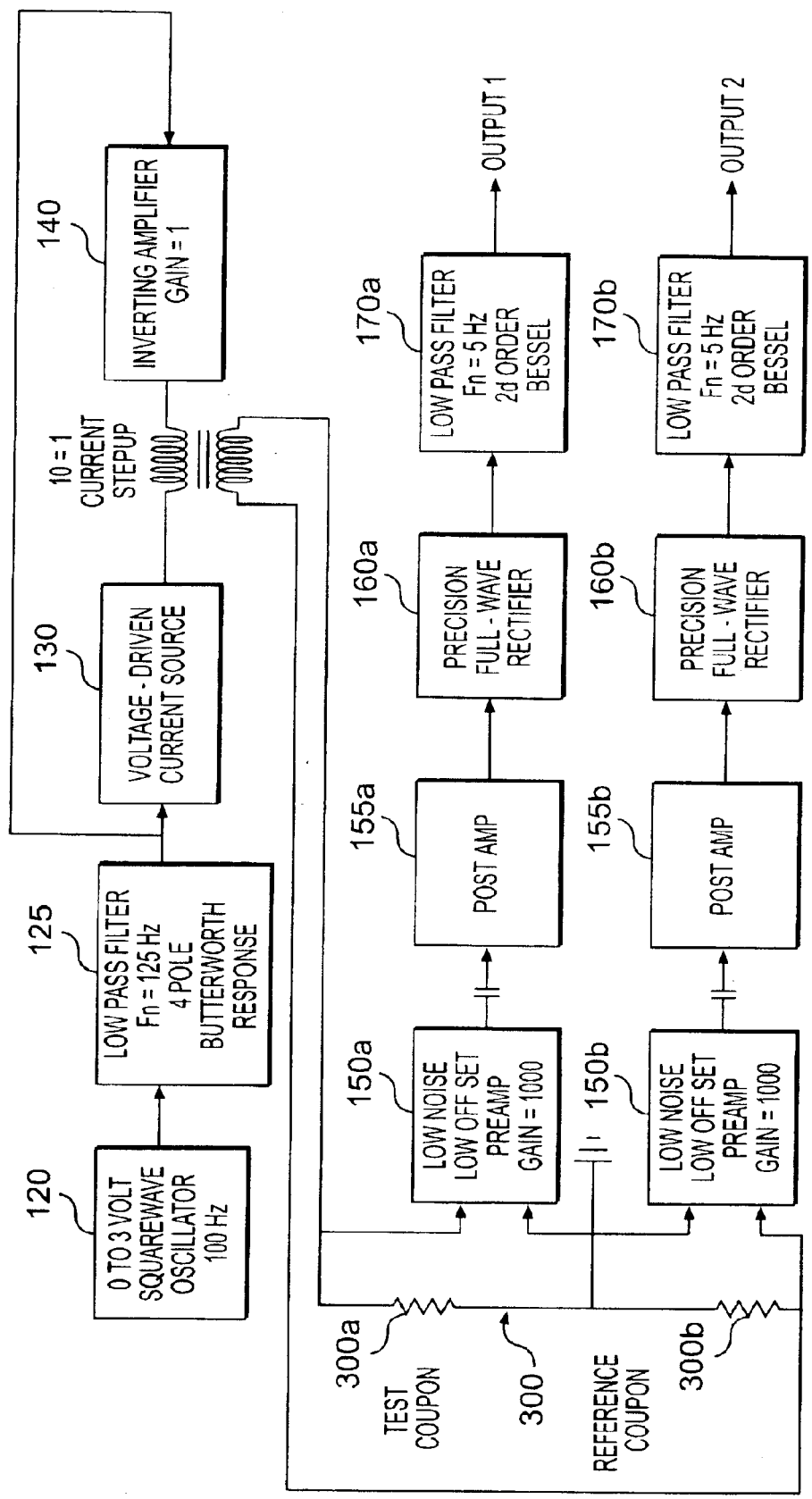
FIG. 1 is a block diagram of an exemplary implementation of an embodiment of the present invention.
Figure 2:
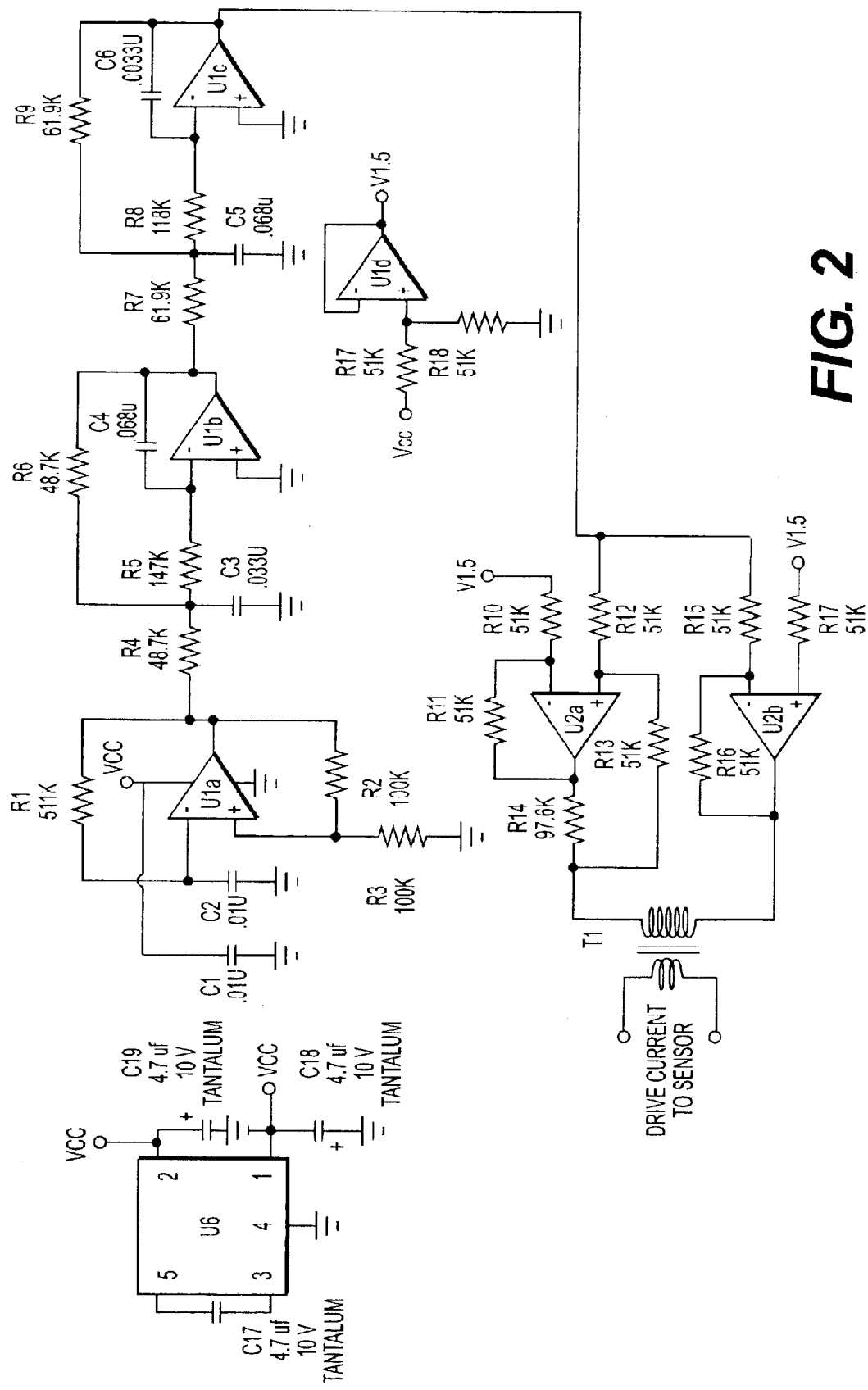
FIG. 2 is a schematic diagram of the exemplary implementation of FIG. 1, in accordance with the present invention.
Figure 2:
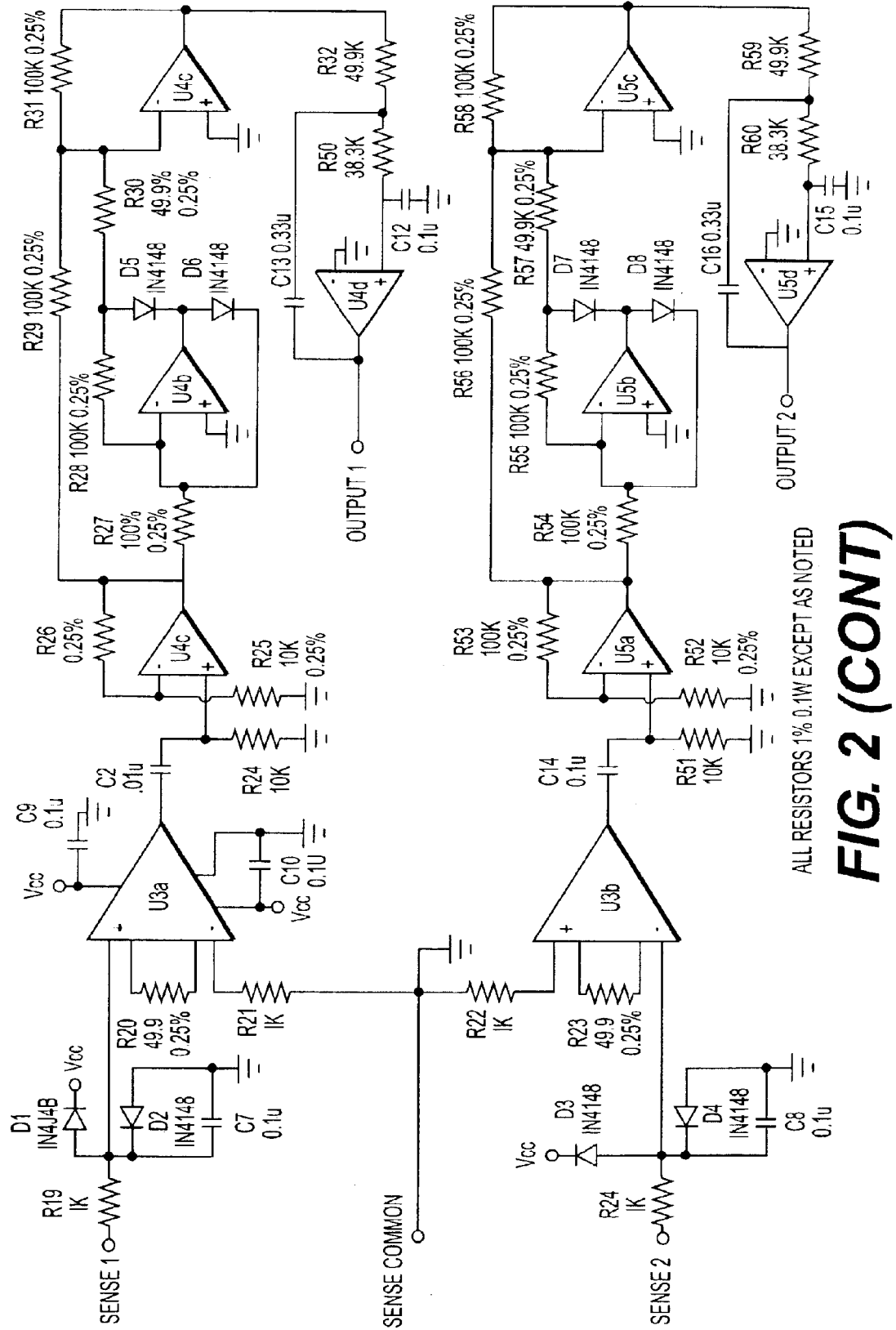

Reference is now made to FIGS. 1 and 2, which illustrate, respectively, a block diagram and schematic of a corrosion monitoring implementation of the present invention.

An oscillator 120, preferably a 100 Hz symmetrical hysteretic oscillator using a RRIO (rail-to-rail input and output) opamp, produces a symmetrical square wave oscillating between ground and Vcc. This type of oscillator has the advantage over sine wave oscillators, such as Wein bridge, state-variable, phase shift or twin-tee oscillators, of starting immediately at full magnitude. Thus, an oscillator of the kind depicted minimizes the total time required from application of power to availability of stable measurement data. The present inventors have determined that post-filtering such a square wave signal provides much faster response than was possible with alternatives while providing acceptable spectral purity. Oscillator 120 is comprised of U1a and associated circuitry. The rationale for selection of the 100 Hz frequency is described below. It is noted that other oscillating frequencies may be selected depending on the particular application.

The resulting square wave is filtered by, in this particular exemplary implementation, a $4^{th}$-order Butterworth-response low pass filter 125 comprised of U1b, U1c and associated circuitry. The corner frequency of this filter is 125 Hz. The filtered output is a sine wave with no second harmonic component because it is symmetrical, and it has less than 1% third-harmonic component. The output sinusoid is stable to within less than 0.1% of steady state magnitude within fewer than 200 milliseconds. Those skilled in the art will appreciate that other types of filters may be employed instead of the Butterworth type and that the present invention should not, therefore, be construed to be limited to this type of filter. The choice of response and order of the filter is governed by desired spectral purity versus rapidity of response and freedom from overshoot upon startup.

The sinusoidal voltage thus produced is presented to a voltage-driven current source 130 comprised of U2a and associated circuitry. It drives its load with a sinusoidal current of 5 mA peak regardless of load impedance or voltage required to produce the intended current. The current source is referenced to ½ Vcc so it provides AC current as the drive voltage varies sinusoidally and symmetrically above and below ½ Vcc.

Inverting amplifier 140 (U2b) inverts the sinusoidal voltage with unity gain. This provides differential drive for the primary of transformer 135. The current drive's output voltage can only vary from near Vcc to near ground, but since the other end of the primary of transformer 135 is connected to a voltage source varying out of phase with the drive current, drive voltage can approach ±Vcc in magnitude if necessary to reach peak values of ±5 mA. The actual voltage appearing on the primary of transformer 135 will depend on the resistance of the leads to coupons 300a (the "test" coupon) and 300b (the "reference" coupon), also referred to herein collectively as a "device under test."

Since coupons 300a and 300b are current driven in series, they are excited with identical current. Transformer isolation prevents undesirable ground loop current in the common return.

The test and reference coupons 300a, 300b (also shown in FIG. 3) are Kelvin connected as shown in FIG. 2. As shown, sense voltage preferably returns on wires separate from those conducting the drive current. The drive frequency of 100 Hz was chosen as high enough in frequency to result in a transformer of acceptable size and weight (about 2 $cm^3$ and about 4 grams), but low enough to minimize the effects of coupling between drive wires and sense wires in the wiring between the instrument and the coupons.

The sense voltages from the coupons are supplied to instrumentation pre-amplifiers U3a and U3b, which correspond generally with 150a, 150b. These pre-amplifiers are preferably selected for very low noise and very low DC offset. Low DC offset is desirable to keep the amplifiers out of saturation, given the high gain and the low supply voltage available. They are preferably set to a gain of 1000 (60 dB). Pre-amplifiers 150a, 150b are also preferably arranged such that the phase-opposite voltages from coupons 300a, 300b are amplified in phase to minimize crosstalk, although crosstalk isolation between pre-amplifiers 150a, 150b is believed to exceed 120 dB.

The outputs of pre-amplifiers 150a, 150b are AC-coupled to post amplifiers U4a and U5a, which correspond to elements 155a, 155b. AC coupling is used to remove any amplified DC offset error from the pre-amplifiers.

The post-amplified signals are presented to precision full-wave rectifiers 160a, 160b, comprised of U4b and U5b and associated circuitry. The theory of operation of this block is straightforward and well-documented in the literature. See, e.g., LB-9 (Linear Brief 9) from National Semiconductor, Santa Clara, Calif.

The resulting full-wave rectified signals are low pass filtered by, for example, 2d order Bessel response filters 170a, 170b, comprised of U4d for one channel and U5d for the other channel. In the implementation shown, these are Sallen-Key filters with unity gain regardless of tolerance in resistor values. These filters have a 3 dB corner frequency of 5 Hz. This form of filtering is preferred over the usual R-C post-detection filtering to achieve fast response with good rejection of post-rectification ripple. The DC output of filters 170a, 170b is proportional to the average value of the rectified AC input. The output is settled to within 0.2% within 200 milliseconds of oscillator startup, including delay in the oscillator filter. At 1 volt output, ripple is about 1 mV RMS.

Filters 170a, 170b limit system bandwidth to 5 Hz, which gives the system very good immunity to EMI and to Johnson noise in the low-level stages.

As added protection, the inputs to pre-amplifiers 150a, 150b are preferably protected against transients by resistors followed by diode clamps to ground and Vcc. DC offset from leakage current of the diodes used is negligible over the full MIL temperature range due to the low impedances involved. In addition, in a preferred implementation, the instrumentation opamps used are internally protected for overvoltage up 40 volts.

U6 (FIG. 2) is a charge-pump voltage inverter operating at about 35 KHz to produce a negative bias voltage for the instrumentation opamps. The input signals are typically within less than a millivolt of ground potential so the first stage amplifiers require negative bias. Power supply rejection of these amplifiers exceeds 120 dB at the frequencies of interest and the 5 Hz lowpass filters eliminates any noise significantly above that frequency, so the negative bias is not regulated.

Figure 3:
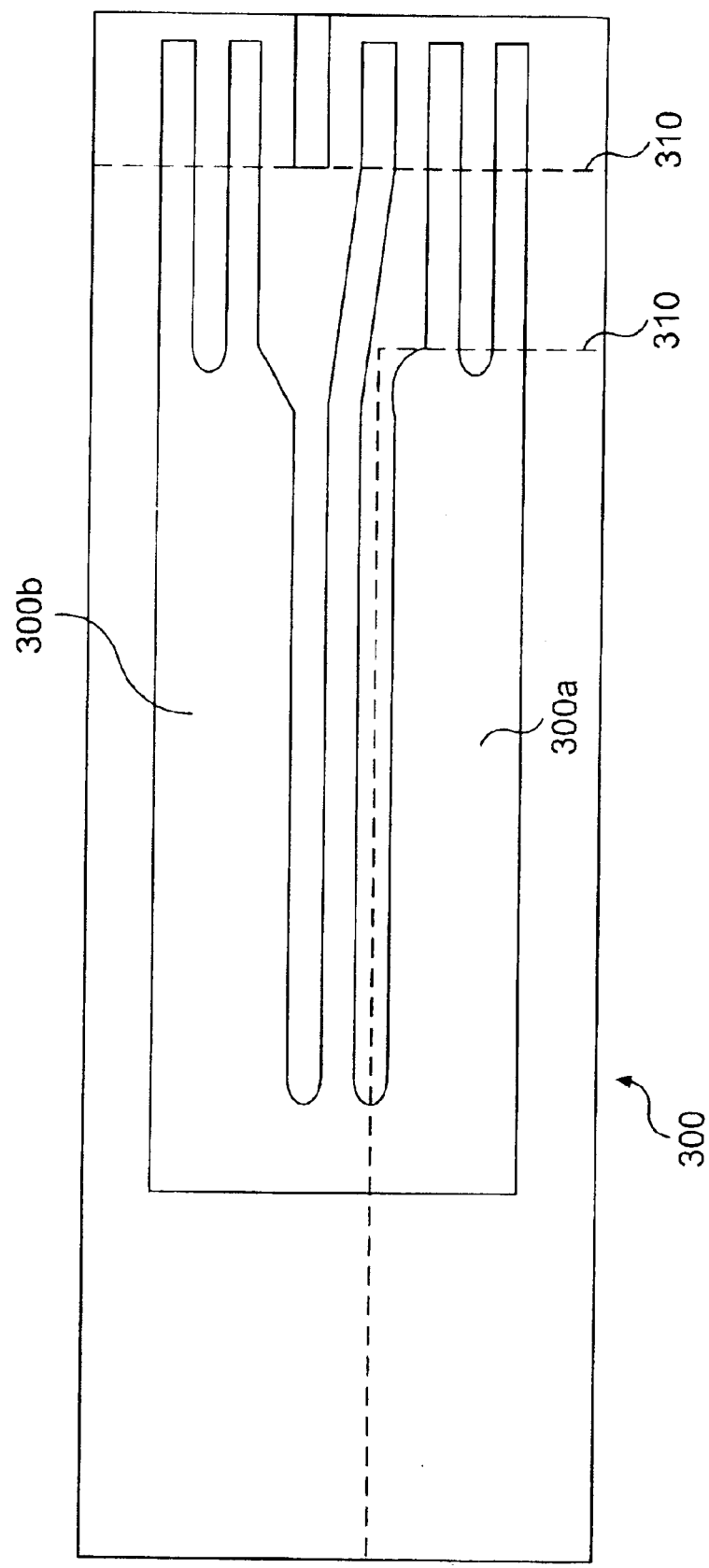
FIG. 3 depicts an exemplary test coupon that may be used in conjunction with the apparatus of the present invention.

FIG. 3 depicts an exemplary coupon 300 that may be used in conjunction with the apparatus of the present invention. Coupon 300 comprises two portions, a test coupon portion 300a and a reference coupon portion 300b. Reference coupon portion 300b and its associated leads are preferably coated with a water tight and air tight coating (the border of which is identified by dashed lines 310) to seal the reference coupon from the ambient environment. Accordingly, only test coupon portion 300a is exposed to the elements and experiences corrosion and corresponding change in resistance that is detected by the apparatus in accordance with the present invention.

As mentioned, the present invention may also be used for straingage applications, or other applications in which milliohm range sensing might be desirable.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A micropower apparatus for low impedance measurements, comprising:
    a voltage-driven current source that is driven by an oscillator that has a square wave output;
    a transformer having a primary and a secondary, the primary of the transformer being connected to the voltage-driven current source, the secondary of the transformer being connectable to a device under test; and
    a detection circuit, the detection circuit comprising an amplification stage, a rectifying stage and a low pass filter stage, the detection circuit also being connected to the secondary of the transformer.

2. The apparatus of claim 1, further comprising a low pass filter disposed between the oscillator and the voltage-driven current source.

3. The apparatus of claim 1, wherein the voltage-driven current source comprises an inverting amplifier with unity gain connected to one side of the primary of the transformer.

4. The apparatus of claim 1, wherein the operating frequency of the oscillator is about 100 Hz.

5. The apparatus of claim 1, wherein the oscillator starts substantially at full magnitude upon application of power.

6. The apparatus of claim 1, further comprising a device under test.

7. The apparatus of claim 6, wherein the device under test comprises a combination test coupon and reference coupon.

8. The apparatus of claim 1, wherein the amplification stage comprises a pre-amplifier stage and a post amplifier stage.

9. The apparatus of claim 1, wherein the transformer comprises a 10:1 step-up transformer.

10. The apparatus of claim 1, wherein the apparatus is capable of milliohm detection.

11. An apparatus for environmental monitoring, comprising:
    a drive circuit and a monitoring circuit;
    the drive circuit comprising:
        a stepup current transformer; and
        a square wave oscillator feeding a primary of the transformer via a low pass filter and voltage-driven current source;
    the monitoring circuit comprising:
        a pair of low noise, low offset pre-amplifiers;
        a pair of post amplifiers connected to outputs of the pair of pre-amplifiers;
        a pair of full wave rectifiers connected to outputs of the pair of post amplifiers; and
        a pair of low pass filters connected to the outputs of the pair of full-wave rectifiers,
    wherein the drive circuit and monitoring circuit are connected to each other when a test coupon and a reference coupon are connected therebetween.

12. The apparatus of claim 11, further comprising an inverting amplifier having unity gain connected to the low pass filter of the drive circuit and one side of the primary of the transformer.

13. The apparatus of claim 11, wherein a secondary of the transformer is in electrical connection with inputs of the monitoring circuit.

14. The apparatus of claim 11, wherein the drive circuit drives the test coupon and the reference coupon, and the monitoring circuit detects, ratiometrically, characteristics of the test and reference coupons.

15. The apparatus of claim 14, wherein the characteristics comprise electrical resistance.

16. The apparatus of claim 11, wherein a device under test is driven by the drive circuit and simultaneously monitored by the monitoring circuit.

17. The apparatus of claim 11, wherein the square wave oscillator oscillates at a frequency of about 100 Hz.

18. The apparatus of claim 11, further comprising a charge-pump voltage inverter for supplying a negative voltage to at least the pair of pre-amplifiers.

19. A method of monitoring an environment, comprising:
    driving a series arranged and Kelvin connected test coupon and reference coupon with an AC current; and
    monitoring, ratiometrically, characteristics of the test and reference coupons to determine a state of the environment,
    wherein the step of driving comprises driving a stepup current transformer with a square wave that has been low pass filtered, and
    wherein the step of monitoring comprises pre-amplifying a voltage signal measured across the test and reference coupons, further amplifying the voltage signal, full wave rectifying the voltage signal, and low pass filtering a result of the full-wave rectifying step.

20. The method of claim 19, further comprising driving a first side of a primary of the transformer with a voltage-driven current source.

21. The method of claim 19, wherein the characteristics comprise electrical resistance.

22. The method of claim 19, wherein the square wave oscillates at a frequency of about 100 Hz.

23. The method of claim 19, further comprising employing a charge-pump voltage inverter to supply a negative supply voltage.

* * * * *